(12) United States Patent
Shchegrov et al.

(10) Patent No.: US 9,400,246 B2
(45) Date of Patent: Jul. 26, 2016

(54) OPTICAL METROLOGY TOOL EQUIPPED WITH MODULATED ILLUMINATION SOURCES

(71) Applicant: KLA-Tencor Corporation, Milpitas, CA (US)

(72) Inventors: Andrei V. Shchegrov, Campbell, CA (US); Lawrence D. Rotter, Pleasanton, CA (US); David Y. Wang, Santa Clara, CA (US); Andrei Veldman, Sunnyvale, CA (US); Kevin Peterlinz, Fremont, CA (US); Gregory Brady, San Jose, CA (US); Derrick Shaughnessy, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 289 days.

(21) Appl. No.: 13/648,768

(22) Filed: Oct. 10, 2012

(65) Prior Publication Data

US 2013/0169966 A1    Jul. 4, 2013

Related U.S. Application Data

(60) Provisional application No. 61/545,965, filed on Oct. 11, 2011.

(51) Int. Cl.
*G01J 4/00*    (2006.01)
*G01N 21/55*    (2014.01)
(Continued)

(52) U.S. Cl.
CPC ............ *G01N 21/55* (2013.01); *G01B 11/0616* (2013.01); *G01N 21/4738* (2013.01); *G03F 7/70608* (2013.01); *G03F 7/70625* (2013.01); *G03F 7/70633* (2013.01)

(58) Field of Classification Search
CPC .............. G01N 21/4738; G01N 21/55; G03F 7/70633; G03F 7/70608; G03F 7/70625; G01B 11/0616

USPC .................................................. 356/369, 445
See application file for complete search history.

(56) References Cited

U.S. PATENT DOCUMENTS 5,548,404 A  *  8/1996  Kupershmidt et al. ....... 356/368
5,739,909 A      4/1998  Blayo et al.
(Continued)

FOREIGN PATENT DOCUMENTS

CN    101207957 A    6/2008
CN    101779117 A    7/2010

OTHER PUBLICATIONS

Guillaumond et al., Comparison of Two Flattening Techniques on a Double-Pass Erbium-Doped Superfluorescent Fiber Source for Fiber-Optic Gyroscope, IEEE Journal on Selected Topics in Quantum Electronics, vol. 7, No. 1, Jan./Feb. 2001, pp. 17-21.
(Continued)

*Primary Examiner* — Tarifur Chowdhury
*Assistant Examiner* — Sunghee Y Gray
(74) *Attorney, Agent, or Firm* — Suiter Swantz pc llo

(57) ABSTRACT

The present invention may include a modulatable illumination source configured to illuminate a surface of a sample disposed on a sample stage, a detector configured to detect illumination emanating from a surface of the sample, illumination optics configured to direct illumination from the modulatable illumination source to the surface of the sample, collection optics configured to direct illumination from the surface of the sample to the detector, and a modulation control system communicatively coupled to the modulatable illumination source, wherein the modulation control system is configured to modulate a drive current of the modulatable illumination source at a selected modulation frequency suitable for generating illumination having a selected coherence feature length. In addition, the present invention includes the time-sequential interleaving of outputs of multiple light sources to generate periodic pulses trains for use in multi-wavelength time-sequential optical metrology.

24 Claims, 10 Drawing Sheets

(51) Int. Cl.
*G01B 11/06* (2006.01)
*G01N 21/47* (2006.01)
*G03F 7/20* (2006.01)

(56) References Cited

U.S. PATENT DOCUMENTS

| | | |
|---|---|---|
| 6,297,880 B1 | 10/2001 | Rosencwaig et al. |
| 6,339,471 B1 | 1/2002 | Morita |
| 6,429,943 B1 | 8/2002 | Opsal et al. |
| 6,600,590 B2 | 7/2003 | Roddy et al. |
| 6,665,131 B2 | 12/2003 | Suzuki et al. |
| 7,357,513 B2 | 4/2008 | Watson et al. |
| 7,435,982 B2 | 10/2008 | Smith |
| 7,567,351 B2 | 7/2009 | Opsal et al. |
| 8,441,639 B2 | 5/2013 | Kandel et al. |
| 8,896,832 B2 | 11/2014 | Hill et al. |
| 2002/0154375 A1 | 10/2002 | Roddy et al. |
| 2006/0215716 A1 | 9/2006 | Luo et al. |
| 2009/0153825 A1 | 6/2009 | Edart et al. |
| 2009/0259098 A1 | 10/2009 | Krattiger |
| 2009/0304033 A1 | 12/2009 | Ogilvy et al. |
| 2010/0067555 A1* | 3/2010 | Austin et al. ............... 372/25 |
| 2010/0165345 A1* | 7/2010 | Bruls et al. ............... 356/436 |
| 2010/0271621 A1 | 10/2010 | Levy et al. |
| 2010/0309477 A1 | 12/2010 | Yun et al. |
| 2010/0315650 A1* | 12/2010 | Olszak ............... 356/498 |
| 2011/0069312 A1 | 3/2011 | Kandel et al. |
| 2011/0310388 A1 | 12/2011 | Hill et al. |

OTHER PUBLICATIONS

P.S. Hauge, Mueller matrix ellipsometry with imperfect compensators, Journal of the Optical Society of America, vol. 68, Issue 11, pp. 1519-1528, Nov. 1978.

R.M.A. Azzam, A simple Fourier photopolarimeter with rotating polarizer and analyzer for measuring Jones and Mueller matrices, Optics Communications, vol. 25, Issue 2, May 1978, pp. 137-140, Elsevier.

M.L. Aleksandrov et al., Method and apparatus for complete ellipsometry (review), Journal of Applied Spectroscopy, Jun. 1986, vol. 44, Issue 6, pp. 559-578, Kluwer Academic Publishers-Plenum Publishers.

* cited by examiner

OPTICAL METROLOGY TOOL EQUIPPED WITH MODULATED ILLUMINATION SOURCES

CROSS-REFERENCE TO RELATED APPLICATION

The present application is related to and claims the benefit of the earliest available effective filing date(s) from the following listed application(s) (the "Related applications") (e.g., claims earliest available priority dates for other than provisional patent applications or claims benefits under 35 USC §119(e) for provisional patent applications, for any and all parent, grandparent, great-grandparent, etc. applications of the Related application(s)).

RELATED APPLICATIONS

For purposes of the USPTO extra-statutory requirements, the present application constitutes a regular (non-provisional) patent application of United States Provisional patent application entitled An Optical Metrology Tool Using Modulated Light Sources, naming Andrei Shchegrov, Lawrence D. Rotter, David Y. Wang, Andrei Veldman, Kevin Peterlinz, Gregory Brady, and Derrick A. Shaughnessy as the inventors, filed Oct. 11, 2011, Application Ser. No. 61/545,965.

TECHNICAL FIELD

The present invention generally relates to a method and system for optical metrology, and, in particular, a method and system for optical metrology with time-modulated illumination sources.

BACKGROUND

As demand for ever-shrinking semiconductor device features continues to increase so too will the demand for improved optical meteorological techniques. Optical metrology techniques may include critical dimension (CD) metrology, thin film thickness and composition metrology, and overlay metrology. These optical metrology techniques may be carried out utilizing a variety of optical architectures including scatterometry-based optical systems, reflectometry-based optical systems, ellipsometry-based optical systems, and spectrometry-based optical systems.

Typically, optical metrology systems utilize light sources operating in a constant-current or in a constant-light-output mode in order to ensure optical stability of the system as well as keeping noise levels within tolerated limits.

In optical metrology settings where coherent light sources are implemented, the production of coherent artifacts, such as interference fringes resulting from duplicate images (i.e., "ghosts) and speckle, are significant concerns in the operation of the given optical metrology tool. Due to the large coherence length of laser-based illumination sources, minimizing the impact of coherent artifacts can be challenging. Coherent artifacts manifest in optical metrology settings where the coherence length, often 100 m or more, of the utilized illumination is larger than the distance between light reflecting surfaces of the metrology tool. Such reflecting surfaces may include lenses, beam splitters, optical fibers and the like. In this scenario, a primary beam will constructively interfere with illumination from a parasitic beam, leading to the production of ghost induced interference fringes. The interference contributions may grow to such a degree that they possess intensity values on the same order of magnitude of the primary beam, thereby severely hampering the usability of the given optical metrology tool.

In addition, some metrology applications require time-sequencing intensity control of multiple illumination sources emitting different wavelengths of light. The prior art accomplishes time-sequencing intensity control utilizing various optical-mechanical and electro-optic device such as shutters, acousto-optic devices, Pocket's cells, and the like. The prior art uses of such devices to control the time-sequencing of multiple illumination sources may lead to reduced stability and repeatability.

Therefore, it would be advantageous to cure the shortfalls of the prior art and provide a system and method for mitigating the effects of coherence artifacts and additional noise sources in an optical metrology setting. In addition, it would be advantageous to produce a system and method providing an efficient means for time-sequencing of multi-wavelength illumination source outputs for multi-wavelength optical metrology applications.

SUMMARY

An optical metrology tool is disclosed. In one aspect, the optical metrology tool may include, but is not limited to, a modulatable illumination source configured to illuminate a surface of a sample disposed on a sample stage; a set of illumination optics configured to direct illumination from the modulated illumination source to the surface of the sample; a set of collection optics; a detector configured to detect at least a portion of illumination emanating from a surface of the sample, wherein the set of collection optics is configured to direct illumination from the surface of the sample to the detector; and a modulation control system communicatively coupled to the modulatable illumination source, wherein the modulation control system is configured to modulate a drive current of the modulatable illumination source at a selected modulation frequency suitable for generating illumination having a selected coherence feature.

In another aspect, the optical metrology tool may include, but is not limited to, a first illumination source configured to generate illumination of a first wavelength; at least one additional illumination source configured to generate illumination of an additional wavelength, the additional wavelength different from the first wavelength, the first illumination source and the at least one additional illumination source configured to illuminate a surface of a sample disposed on a sample stage; a set of illumination optics configured to direct illumination of the first wavelength and illumination of the at least one additional wavelength from the first illumination source and the at least one additional illumination source to the surface of the sample; a set of collection optics; a detector configured to detect at least a portion of illumination emanating from a surface of the sample, wherein the set of collection optics is configured to direct illumination emanating from the surface of the sample to the detector; and a modulation control system communicatively coupled to the first illumination source and the at least one additional illumination source, wherein the modulation control system is configured to modulate a drive current of the first illumination source in order to generate a first illumination waveform of the first wavelength, wherein the modulation control system is configured to modulate a drive current of the at least one additional illumination source in order to generate an additional illumination waveform of the additional wavelength, wherein pulses of the first illumination waveform are interleaved in time with at least pulses of the additional illumination waveform, the first illumination waveform and the additional illumination waveform having a selected waveform frequency.

In another aspect, the optical metrology tool may include, but is not limited to, a first illumination source configured to generate illumination of a first wavelength; at least one additional illumination source configured to generate illumination of an additional wavelength, the additional wavelength different from the first wavelength, the first illumination source and the at least one additional illumination source configured to illuminate a surface of a sample disposed on a sample stage; a set of illumination optics configured to direct illumination of the first wavelength and illumination of the at least one additional wavelength from the first illumination source and the at least one additional illumination source to the surface of the sample; a set of collection optics; a detector configured to detect at least a portion of illumination emanating from a surface of the sample, wherein the set of collection optics is configured to direct illumination emanating from the surface of the sample to the detector; a first illumination switching device optically coupled to the first illumination source, wherein the first illumination switching device is configured to control transmitted intensity of the illumination of the first wavelength; at least one additional illumination switching device optically coupled to the at least one additional illumination source, wherein the at least one additional illumination switching device is configured to control transmitted intensity of the illumination of the additional wavelength; and an illumination control system communicatively coupled to the first illumination switching device and the at least one additional switching device, wherein the illumination control system is configured to modulate transmitted intensity of the illumination of the first wavelength and transmitted intensity of the illumination of the additional wavelength by controlling one or more characteristics of the illumination switching device.

In another aspect, the optical metrology tool may include, but is not limited to, a modulatable pumping source configured to generate illumination beam; a plasma cell, the plasma cell including a bulb for containing a volume of gas; a set of optical elements configured to shape the illumination beam and focus the illumination beam from the modulatable pumping source into the volume of gas in order to maintain a plasma within the volume of gas; a set of illumination optics configured to direct the illumination beam from the plasma cell to the surface of a sample; a set of collection optics; a detector configured to detect at least a portion of illumination emanating from a surface of a sample, wherein the set of collection optics is configured to direct illumination from the surface of the sample to the detector; a pump control system communicatively coupled to the modulatable pumping source, wherein the pump control system is configured to modulate a drive current of the modulatable pumping source at a selected modulation frequency in order to produce time-varying characteristics within the plasma contained within the plasma cell.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Figure 1:
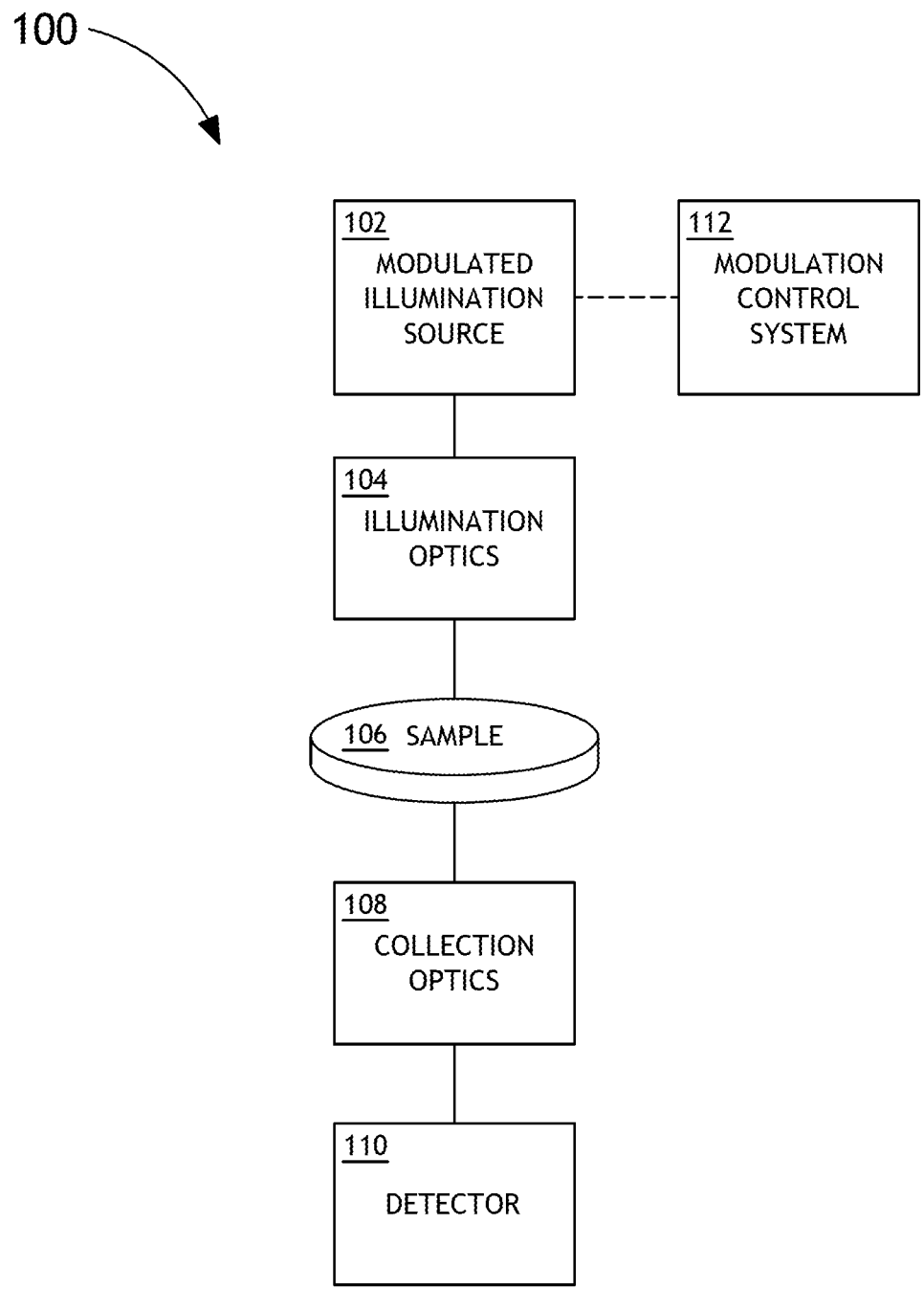
FIG. 1 illustrates a high level block diagram view of an optical metrology tool with one or more modulated illumination sources, in accordance with one embodiment of the present invention.

Reference will now be made in detail to the subject matter disclosed, which is illustrated in the accompanying drawings.

Referring generally to FIGS. 1 through 7B, an optical metrology tool having time-modulated illumination source capabilities is described in accordance with the present invention. The present disclosure is directed toward systems and methods for performing optical metrology with one or more time-modulated illumination sources. The time-modulation of illumination emanating from one or more illumination sources of the metrology system of the present invention provides for improved precision, accuracy, and metrology throughput. The implementation of illumination modulation provided by the present invention aids in the suppression of coherence artifacts, such as, but not limited to, interference fringes, coherent noise, and speckle, in measured optical signals (e.g., angular-resolved reflectivities or ellipsometric parameters, polarization-resolved reflectivities or ellipsometric parameters, wavelength-resolved reflectivities or ellipsometric parameters, and the like). In addition, the present invention is further directed to the time-modulation of illumination output of one or more pumping sources of a light-sustained plasma light source. The modulation of pumping source illumination output provides for a reduction of noise levels in output illumination of the sustained plasma light source.

Those skilled in the art will recognize that coherence artifact control is a common challenge in designing an optical metrology tool. In settings where a given optical metrology tool includes one or more coherent light sources (e.g., lasers), the ability to control the coherent effects (e.g., speckle and interference fringes) associated with stray light and ghosts becomes increasingly difficult. For example, a given optical metrology tool (see FIGS. 2A and 2B) includes multiple optical surfaces. These optical surfaces may include, but are not limited to, beamsplitters, lenses, optical fibers, objective lens surfaces, apodizers and the like. Coherent illumination in optical metrology tools often results in detrimental speckle, fringes, and other coherent artifacts. These can contribute to measurement noise and instabilities, leading to degradation in precision and accuracy of the measurement.

For example, in a given optical system a beam propagating through a primary path may interfere with a parasitic beam reflected off an optical surface (e.g., mirror, beam splitter, and the like) of the optical system. To illustrate the detrimental effects of primary beam and parasitic beam interference, the primary beam and the parasitic beam are characterized by intensities $I_1$ and $I_2$. The superposition of these two beams provides a combined beam output as follows:

$$I = I_1 + I_2 + 2\sqrt{I_1 I_2} \cos \varnothing \quad (\text{Eq. 1})$$

where $\varnothing$ represents the relative phase between the primary beam and the parasitic beam from a reflective surface of the optical metrology tool. For illustrative purposes, in a scenario where $I_1=1$ and $I_2=0.0025$ (consistent with a parasitic beam reflecting off a surface with 0.25% reflectivity), the interference term of Eq. 1 will have a magnitude of 10% of the primary beam in instances where the primary and the parasitic wave interfere constructively. This level of interference contribution is unacceptable in most optical metrology tools.

In contrast, in settings where the primary beam and parasitic beam are not coherent with each other, the interference term of Eq. 1 goes to zero and the ghost correction for the metrology tool will have a magnitude of 0.25% of the primary beam, which is significantly more manageable than the case described above.

Those skilled in the art will recognize that a typical spectrum of a laser (e.g., laser based on semiconductor diode technology) includes a single narrow spectral line or multiple narrow spectral lines. Such laser sources commonly have long coherence lengths. Due to their wavelength stability and low noise often single-wavelength laser are utilized ubiquitously throughout metrology applications. Due to the large coherence lengths of single-wavelength lasers, often exceeding 100 m, suppression of coherence artifacts during implementation in a metrology setting for the reasons set forth previously herein.

FIG. 1 illustrates a block diagram view of an optical metrology tool 100 equipped with time-modulated illumination capabilities, in accordance with one embodiment of the present invention. In one aspect of the present invention, the system 100 includes a modulated illumination source 102 configured to illuminate a surface of a sample 106 (e.g., semiconductor wafer) disposed on a sample stage, a detector 110 configured to detect light reflected from the surface of the sample 106, and an optical system, which acts to optically couple the modulated illumination source 102 and the detector 110. The optical system may include a set of illumination optics 104 (e.g., lenses, mirrors, filters, and the like) suitable for directing and/or focusing light from the illumination source 102 to the sample 106. The optical system may further include a set of collection optics 108 (e.g., lenses, mirrors, filters, and the like) suitable for directing light reflected or scattered from the surface of the wafer 106 to the detector 110. In this manner, light may emanate from the illumination source 102 and travel along the illumination arm (via illumination optics 104) to the surface of the sample 106. Light reflected or scattered from the sample 106 may then travel from the surface of the sample 106 to the detector 110 along the collection arm (via collection optics 108) of the system 100. In another aspect, the optical metrology system 100 includes a modulation control system 112 configured to modulate a drive current of the modulatable illumination source 102 (e.g., laser) at a selected modulation frequency.

It is noted herein that the optical metrology system 100 of the present invention may be configured to carry out any form of optical metrology known in the art. For example, the optical metrology system 100 is configured to perform at least one of the following metrology methodologies: critical dimension (CD) metrology, thin film (TF) thickness and composition metrology, and overlay metrology.

It is further noted herein that the optical metrology system 100 of the present invention is not limited to a particular optical configuration or optical metrology function. In some embodiments, the optical metrology system 100 of the present invention may be configured as a reflectometry-based metrology system. For example, the optical metrology system 100 may include, but is not limited to, a beam profile reflectometer (e.g., narrow band beam profile reflectometer) operating in angle-resolved mode, a spectroscopic reflectometer, and the like. Spectral and single-wavelength beam profile reflectometry are generally described in U.S. Pat. No. 6,429,943, filed on Mar. 27, 2001, which is incorporated herein by reference in the entirety.

In other embodiments, the optical metrology system 100 of the present invention may be configured as a scatterometry-based metrology system. For example, the optical metrology system 100 may include, but is not limited to, a broadband scatterometer (e.g., broadband spectroscopic scatterometer) or a narrow band scatterometer.

In additional embodiments, the optical metrology of the present invention may be configured as an ellipsometry-based metrology system. For example, the optical metrology system 100 may include, but is not limited to, a beam profile ellipsometer or a spectroscopic ellipsometer. An overview of ellipsometry of the principles of ellipsometry is provided generally in Harland G. Tompkins and Eugene A. Irene, *Handbook of Ellipsometry*, 1st ed, William Andrew, Inc., 2005, which is incorporated herein by reference in the entirety. In addition, Mueller matrix ellipsometry is discussed in detail in P. S. Hauge, *Mueller Matrix Ellipsometry with Imperfect Compensators*", J. of the Optical Soc. of Am. A 68(11), 1519-1528, 1978; R. M. A Azzam, *A Simple Fourier Photopolarimeter with Rotating Polarizer and Analyzer for Measuring Jones and Mueller Matrices*, Opt Comm 25(2), 137-140, 1978; which are incorporated herein by reference in their entirety. Further, the concept of "complete" ellipsometry is discussed in M. L. Aleksandrov, et. al. "*Methods and Apparatus for Complete Ellipsometry (review)*", J. Appl. Spectroscopy 44(6), 559-578, 1986, which is incorporated herein in its entirety. Spectral ellipsometry is generally described in U.S. Pat. No. 5,739,909, filed on Oct. 10, 1995, which is incorporated herein by reference in the entirety. Beam profile ellipsometry is generally described in U.S. Pat. No. 6,429,943, filed on Mar. 27, 2001, which has been incorporated previously herein in its entirety.

Figure 2A:
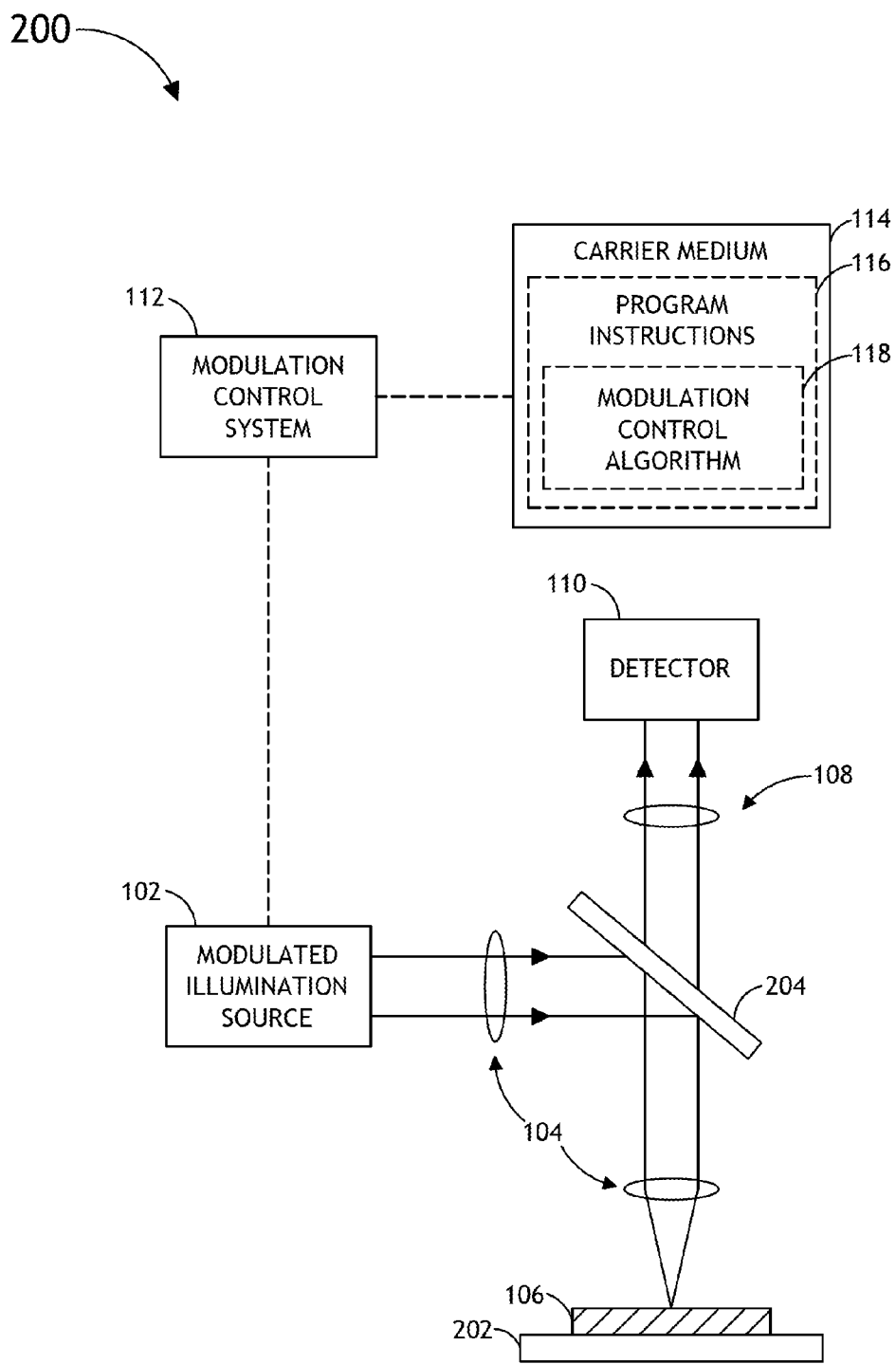
FIG. 2A illustrates a high level schematic view of a reflectometry-based optical metrology tool with one or more modulated illumination sources, in accordance with one embodiment of the present invention.

Referring now to FIG. 2A, the optical metrology system 100 of the present invention may be embodied as a reflectometry-metrology tool, such as tool 200. FIG. 2A illustrates a high-level schematic view of a reflectometry-based metrology tool suitable for implementation in the present invention. The reflectometer 200 may include an illumination source 102, an optical system, and a detector 110. The optical system may include a set of illumination optics 104, a beam splitter 204, and a set of collection optics 108. In this regard, light may emanate from the illumination source 102 and travel via the illumination optics 104 and beam splitter 204 to the surface of the sample 106 disposed on sample stage 202. Light reflected from the sample 106 may then travel from the surface of the sample 106 to the detector 110 via the collection optics 108. Applicant notes that the configuration illustrated in FIG. 2A is not limiting and is provided merely for purposes of illustration. As noted previously, it is anticipated that numerous reflectometer-based optical configurations may be utilized within the scope of the present invention.

Figure 2B:
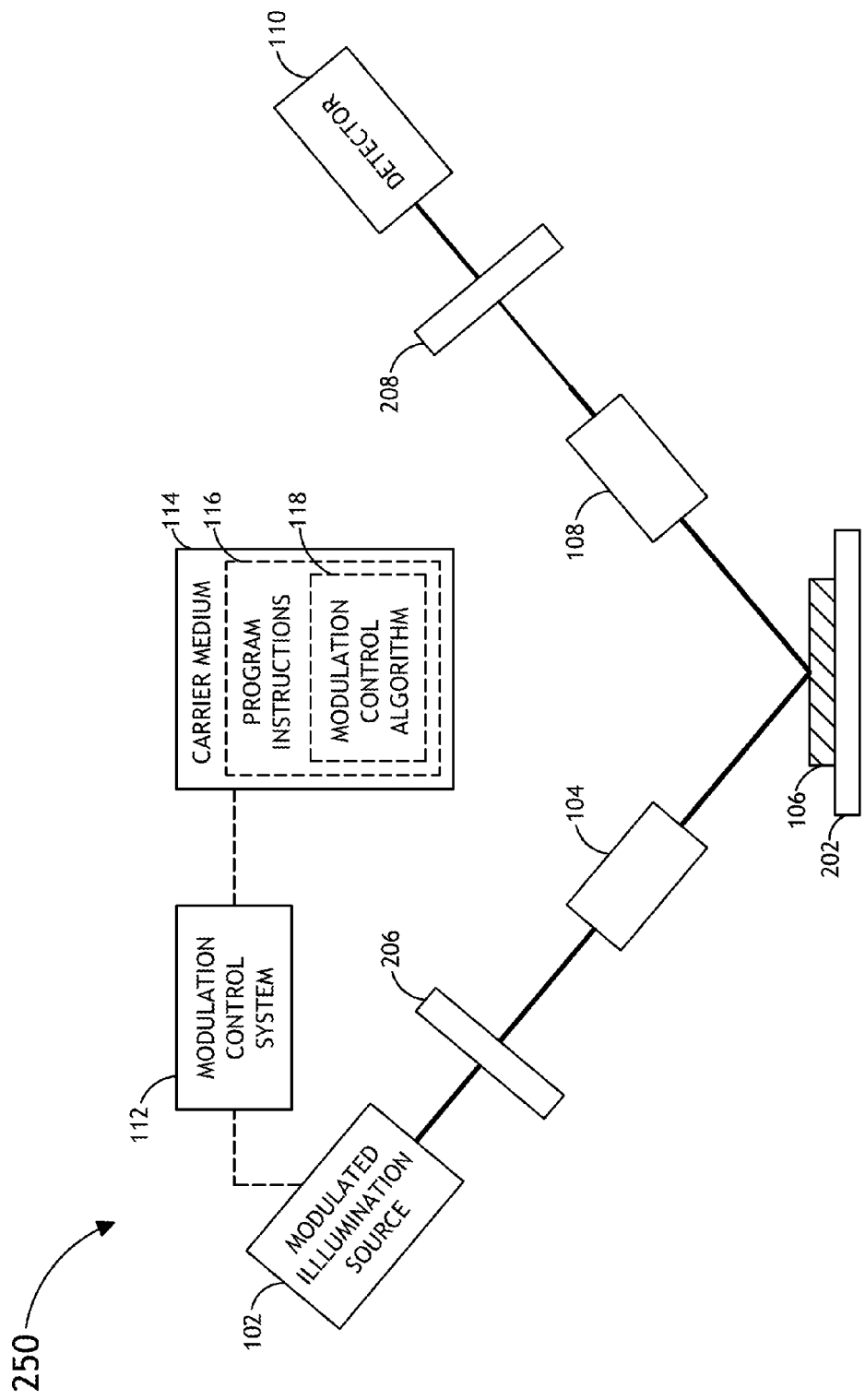
FIG. 2B illustrates a high level schematic view of a ellipsometry-based optical metrology tool with one or more modulated illumination sources, in accordance with one embodiment of the present invention.

Referring now to FIG. 2B, the optical metrology system 100 of the present invention may be embodied as a scatterometry/ellipsometry based metrology tool, such as tool 250. FIG. 2B illustrates a high-level schematic view of an ellipsometry-based metrology tool suitable for implementation in the present invention. The scatterometer/ellipsometer 250 may include an illumination source 102, an optical system, and a detector 110. The optical system may include a set of illumination optics 104, a polarizer 206, a set of collection optics 108, and an analyzer 208. The illumination and collection optics may include mirrors, lenses, beamsplitters, compensators, and the like. In this regard, light may emanate from the illumination source 102 and travel through polarizer 206 and illumination optics 104 to the surface of the sample 106 disposed on sample stage 202. Light scattered from the sample 106 may then travel from the surface of the sample 106 to the detector 110 via the collection optics 108 and through the analyzer 208. Applicant notes that the configuration illustrated in FIG. 2B is not limiting and is provided merely for purposes of illustration. As noted previously, it is anticipated that numerous scatterometry- and ellipsometry-based optical configurations may be utilized within the scope of the present invention.

In one aspect of the present invention, the modulation control system 112 is configured to modulate a drive current of the modulatable illumination source 102 at a selected modulation frequency. In one aspect, the selected modulation frequency may be suitable for generating illumination having a selected coherence feature.

In one embodiment, the selected coherence feature may include, but is not limited to, a selected fringe visibility curve. In this regard, the selected modulation frequency may be suitable for generating illumination having a selected fringe visibility curve. In a further embodiment, the selected modulation frequency may be suitable for generating illumination having a fringe visibility curve suitable for achieving coherence artifacts below a selected tolerance level (e.g., a level where coherence artifacts are small enough to allow for operation of the metrology tool 100). In another embodiment, the modulation frequency is suitable for generating a fringe visibility curve configured to suppress generation of interference fringes having an intensity above a selected level (e.g., intensity of interference fringes small enough to allow for operation of metrology tool 100). In yet another embodiment, the modulation frequency is suitable for generating a fringe visibility curve having a set of intensity peaks positioned at distances different from a characteristic optical path length of the optical metrology tool 100. The characteristic optical path length of the optical metrology tool 100 may include a distance between a first reflecting surface of the optical metrology tool and a second reflecting surface of the optical metrology tool. In a further embodiment, the modulation frequency is suitable for generating illumination with a fringe visibility curve substantially different from a fringe visibility curve of the illumination source in an unmodulated state. As described previously herein, by altering the fringe visibility curve of the illumination emitted by the illumination source 102 to a sufficient degree, the impact from coherence artifacts (e.g., speckle and interference fringes) may be eliminated or at least reduced.

In another embodiment, the selected modulation frequency may be suitable for generating illumination having a coherence length below a selected length (i.e., coherence length less than the distance between optical components of the system 100). For example, the selected modulation frequency may be suitable for generating illumination having a coherence length below the coherence length of the illumination source 102 in an unmodulated state (i.e., the coherence length of the illumination source prior to modulation). By way of another example, the selected modulation frequency may be suitable for generating illumination having a coherence length below a characteristic optical length of the optical metrology tool 100. For instance, the selected modulation frequency may be suitable for generating illumination having a coherence length smaller than a distance between a first reflecting surface of the optical metrology tool 100 and a second reflecting surface of the optical metrology tool 100. As described previously herein, by reducing the coherence length of the illumination emitted by the illumination source 102 below the distance between reflecting surface within the metrology tool 100, the impact from coherence artifacts (e.g., speckle and interference fringes) may be eliminated or at least reduced.

In one embodiment of the present invention, the modulation control system 112 may act to drive the current of one or more laser light sources at a selected frequency. For example, the modulation control system 112 may act to modulate the drive current of a laser light source (e.g., multi-longitudinal mode laser light source) in order to achieve a modified fringe visibility curve in the laser light output, whereby the modified fringe visibility curve of the laser light source is adequate for reducing coherence artifacts within the optical metrology tool 100 below a selected tolerance level. By way of another example, the modulation control system 112 may act to modulate the drive current of a laser light source in order to generate illumination having a coherence length below a selected level.

Figure 3:
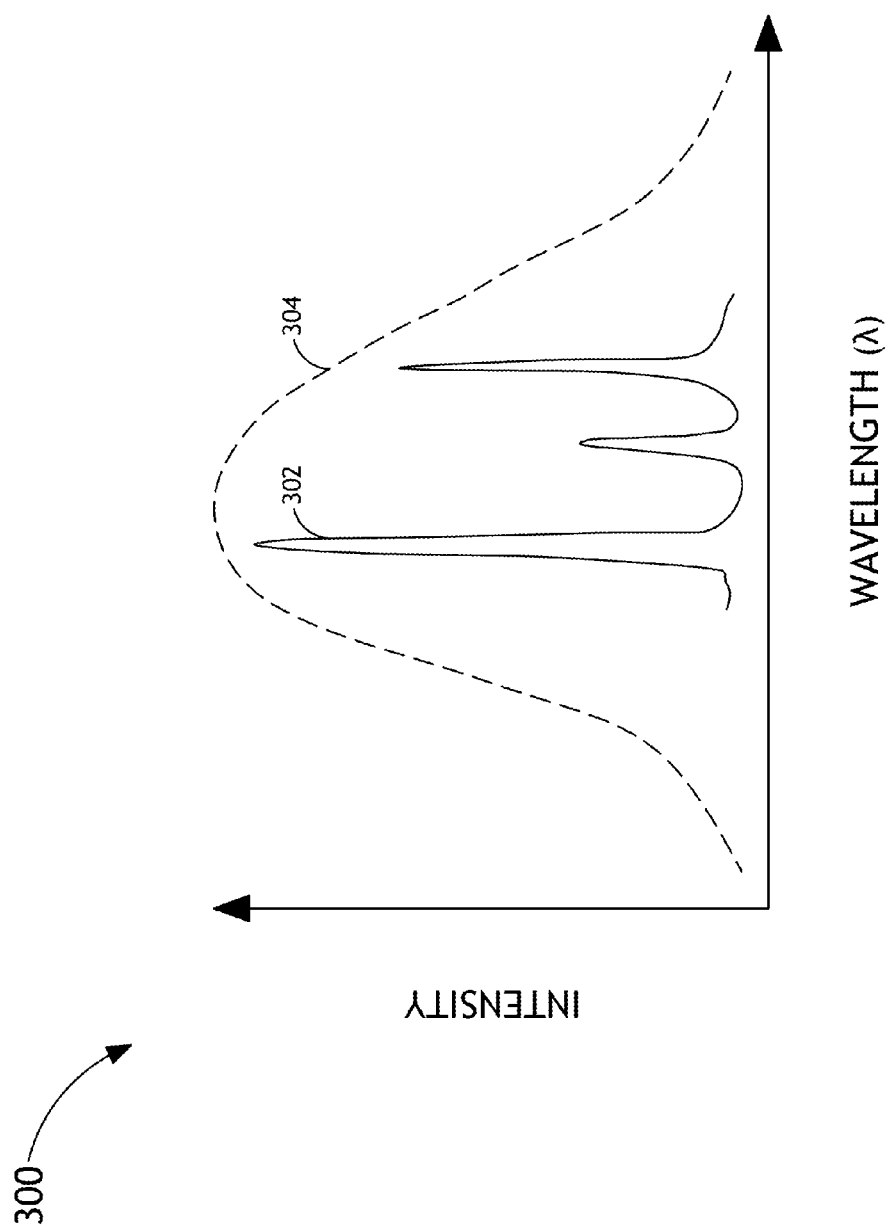
FIG. 3 illustrates a conceptual view of intensity spectra with and without illumination source modulation, in accordance with one embodiment of the present invention.

FIG. 3 illustrates a conceptual view of intensity spectra from a laser source without drive current modulation 302 and intensity spectra from the laser source with drive current modulation 304. As shown in FIG. 3, in the case of D.C. current drive, the spectrum 304 associated with the laser source includes multiple longitudinal modes of the laser cavity. The spectrum 304 illustrated in FIG. 3 represents a broad envelope of the individual spectral peaks of curve 302. In this regard, the fast modulation of the drive current of the laser source results in a broadening and smoothing of the intensity spectrum 304. The alteration of the fringe visibility curve of the laser source aids in suppressing the coherence artifacts (e.g., interference fringes) discussed previously herein. Further, it is noted herein that the optical surfaces of a given optical metrology tool (e.g., 100) may be relatively easily configured so that they are separated by distances sufficient to render the impact of parasitic interference negligible when the illumination source 102 is in the modulated state, such as a state consistent with the intensity spectra 304. Applicant notes that the above description related to fringe visibility curve, coherence length and distance between optical components is presented merely for illustrative purposes and should not be interpreted as limiting.

In a further embodiment, the modulation control system 112 may modulate the drive current of the modulatable illumination source 102 at a frequency in the radio frequency (RF) range. It is further noted herein that the particular frequency at which the control system 112 drives the modulatable illumination source 102 may be selected by trial and error. For instance, the implemented modulation frequency may be a frequency that acts to reduce the coherence length of the illumination from the source 102 below a characteristic optical path length of the optical metrology system 100. For example, the characteristic optical path length of the optical metrology system 100 may include a distance between two or more reflecting surfaces of the optical metrology tool 100. In another instance, it is recognized that neither the coherence length nor the fringe visibility curve (as described above) needs to be measured in order to implement to modulation of the illumination source 102. In this sense, the control system 112 may sweep the modulation frequency of the control system 112 until a satisfactory detector 110 output is achieved.

In a further aspect of the present invention, the modulation control system 112 of the optical metrology tool 100 is equipped with one or more processors (not shown) communicatively coupled to the modulatable illumination source 102 and configured to control the modulation of the illumination source 102. The modulation control system 112 is configured to execute modulation control algorithm 118 stored as a set of program instructions 116 on a carrier medium 114 (e.g., non-transitory storage medium). The program instructions 116 are configured to cause the one or more processors of the control system 112 to carry out one or more of the various steps described in the present disclosure.

It should be recognized that the various control steps associated with the modulation control as described throughout the present disclosure may be carried out by a single computer system or, alternatively, a multiple computer system. Moreover, different subsystems of the system 100 may include a computer system suitable for carrying out at least a portion of the steps described above. Further, the one or more computer systems may be configured to perform any other step(s) of any of the method embodiments described herein.

The modulation control system 112 may include, but is not limited to, a personal computer system, mainframe computer system, workstation, image computer, parallel processor, or any other device known in the art. In general, the term "computer system," "computing system(s)," or "computer control system" may be broadly defined to encompass any device(s) having one or more processors, which execute instructions from a memory medium.

Program instructions 116 implementing methods such as those described herein may be transmitted over or stored on carrier medium 114. The carrier medium 114 may be a transmission medium such as a wire, cable, or wireless transmission link. The carrier medium may also include a non-transitory storage medium such as a read-only memory, a random access memory, a magnetic or optical disk, or a magnetic tape.

In another embodiment, the control system 112 may be communicatively coupled to the illumination source 102 or any other subsystem of system 100 in any manner known in the art. For example, the modulation control system 112 may be communicatively coupled to the various sub-systems of system 100 via a wireline or wireless connection.

In another embodiment of the present invention, the modulatable illumination source 102 may include any narrowband illumination source known in the art. In one embodiment, the illumination source 102 may include, but is not limited to, one or more lasers. For instance, the laser light source may include, but is not limited to, one or more semiconductor lasers. In another example, the laser source may include, but is not limited to, a diode-pumped solid-state laser. In another example, the laser source may include, but is not limited to, a super continuum laser. Further, a first source emitting illumination in a first spectral range may be combined with a second source emitting illumination in a second spectral range.

In another aspect of the present invention, the detector 110 may include any light detection system known in the art suitable for implementation in a reflectometer, scatterometer, spectrometer or ellipsometer setting. For example the detector 110 may include, but is not limited to, at least one of a CCD array, a CMOS array, one-dimensional photodiode array, a two-dimensional photodiode array and the like.

Figure 4A:
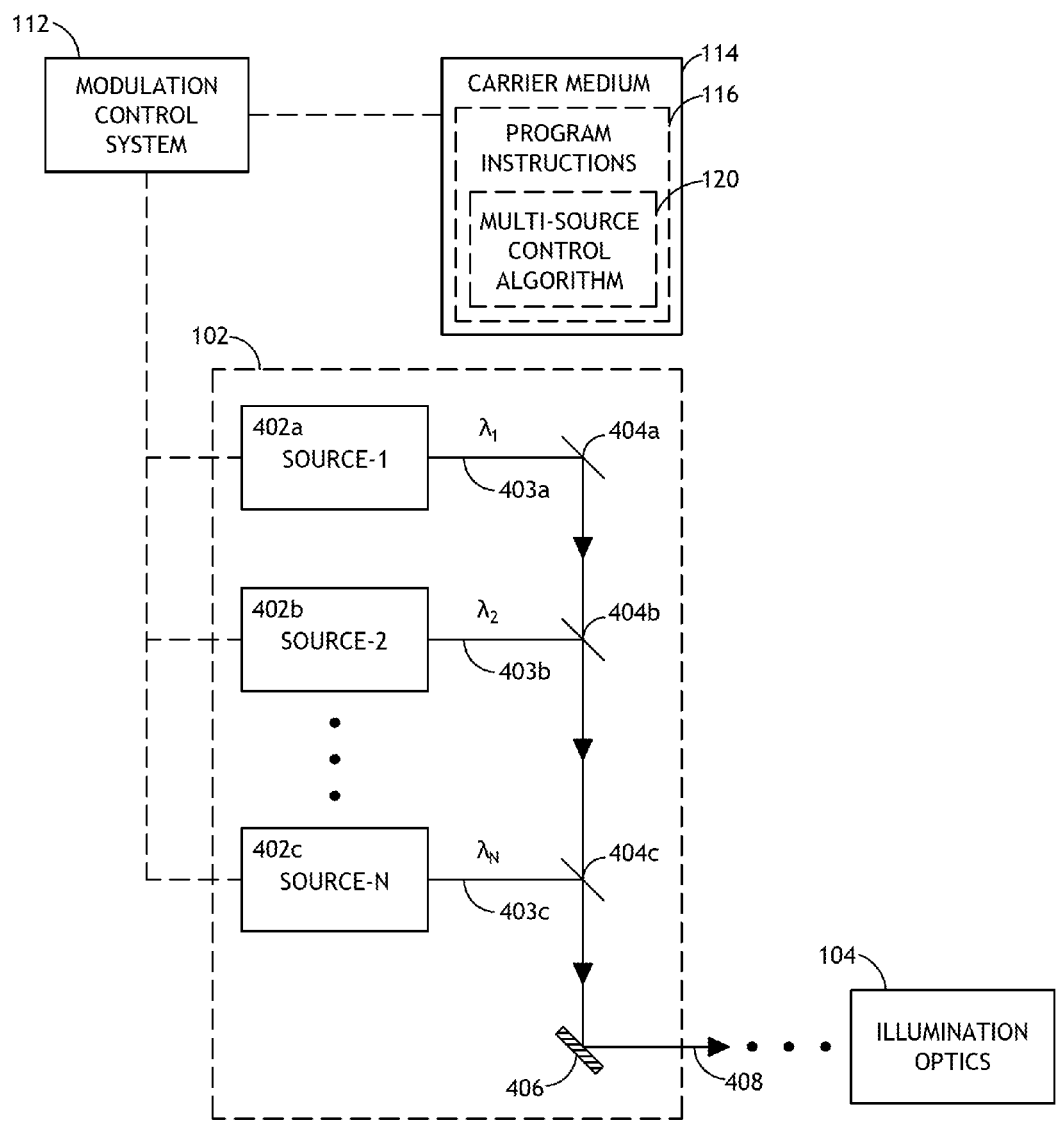
FIG. 4A illustrates a high level schematic view of an optical metrology system equipped with multiple illumination sources each of a different wavelength, in accordance with one embodiment of the present invention.

FIG. 4A illustrates a multi-source illumination source 102, in accordance with an alternative embodiment of the present invention. In one aspect, the multi-source illumination source 102 of the optical metrology tool 100 includes two or more single illumination sources, each single source having a different output wavelength. In one aspect, the present invention provides for stable intensity balance and control of multiple illumination sources. Those skilled in the art will recognize that generally ON/OFF switching of illumination sources, such as lasers and LEDs, may result in reduced stability and lead to an increase in noise. Applicants have found that instability and noise production is limited in settings where periodic waveforms are implemented. In this manner, periodic waveform operation acts to maintain the average stable thermal, electrical, and optical properties of the illumination sources, thereby improving wavelength stability and noise reduction.

In one aspect of the present invention, the modulatable illumination source 102 of the system 100 may include a first illumination source 402a configured to generate illumination of a first wavelength ($\lambda_1$), a second illumination source 402b configured to generate illumination of a second wavelength ($\lambda_2$), and up to, and including, an "Nth" illumination source 402c configured to generate illumination of an Nth wavelength ($\lambda_N$).

In an additional aspect of the present invention, the modulation control system 112 is communicatively coupled to the first illumination source 402a, the second illumination source 402b and up to and including the Nth illumination source 402c by any means known in the art (e.g., wireline or wireless connection). In a further aspect, the modulation control system 112 is configured to execute a multi-source control algorithm 120 suitable for controlling the waveform of illumination output for each of the sources 402a-402c. The modulation control system 112 (via control algorithm 120) is configured to modulate a drive current of the first illumination source 402a in order to generate a first illumination waveform (e.g., step-wise waveform of a selected frequency) of the first wavelength. In addition, the modulation control system 112 is configured to modulate a drive current of the second illumination source 402b in order to generate a second illumination waveform of the second wavelength. In this manner, the pulses of the first illumination waveform are interleaved in time with the pulses of the second illumination waveform, the first illumination waveform and the second illumination waveform having a selected waveform frequency. It is further noted herein that the combined waveform may include any number of component waveforms. In this manner, the pulses of the first illumination waveform are interleaved in time with the pulses of the second illumination waveform and pulses of up to and including the Nth waveform. The interleaving of the various waveforms from the sources 402a-402c allows for time-sequential metrology measurements at multiple wavelengths. Moreover, because the modulation of the illumination from the light sources 402a-402c is accomplished with drive current modulation the present invention obviates the need for various optical-mechanical components such as optical shutters, chopper wheels, and the like. As such, the embodiment illustrated in FIG. 4A provides for a simplified approach to multi-wavelength intensity control in the optical metrology tool 100.

In another embodiment, the multi-source based illumination source 102 may include a plurality of wavelength combiners 404a, 404b, and 404c configured to combine the beams 403a, 403b, and 403c emanating from the illumination sources 402a, 402b, and 402c respectively. In this regard, the wavelength combiners 404a-404c may act to spatially combine the beams, allowing for the temporal interleaving of the source waveforms carried out by the algorithm 120 executed by the modulation control system 112. Following the temporal interleaving and spatial combination of the waveforms into beam, the combined waveform output 408 may be directed to the illumination optics 104 of the optical metrology tool 100. It is further noted that the illumination source 102 may include additional optical elements, such as steering mirror 406. Applicant notes that the optical configuration depicted in FIG. 4A and described above is not limiting and should be interpreted as merely illustrative. It is recognized herein that multiple equivalent optical configurations may be implemented in order to spatially combine and temporally interleave the waveforms of source 402a, source 402b, and up to an including source 402c. The spatial combination of multiple laser beams into a single combined beam is generally described by Hill et al. in U.S. patent application Ser. No. 13/108,892, filed on May 16, 2011, which is incorporated herein in its entirety.

In one embodiment, the modulation of the first, second, and up to and including the Nth illumination sources carried out by the modulation control system 112 may include switching the drive current of a laser-based or LED-based source. Switching of the source drive current in this manner may produce a step-wise (i.e., ON/OFF) or nearly step-wise waveform pattern for the illumination outputs for each of the illumination sources 402a-402c. In this regard, the multi-source approached depicted in FIG. 4A allows for channel selection and relative intensity control in a "color"-sequential manner. For the purposes of the present disclosure, the term "color" is used to describe the primary wavelength (e.g., peak wavelength) of each source. Further, the term "color" should not be interpreted to apply to any particular portion of the electromagnetic spectrum. It is anticipated that the wavelength of a given source may reside well outside the visible spectrum. For instance, the spectral range of the output of sources 402a-402c may include the visible, UV, and IR spectral ranges.

Figure 4B:
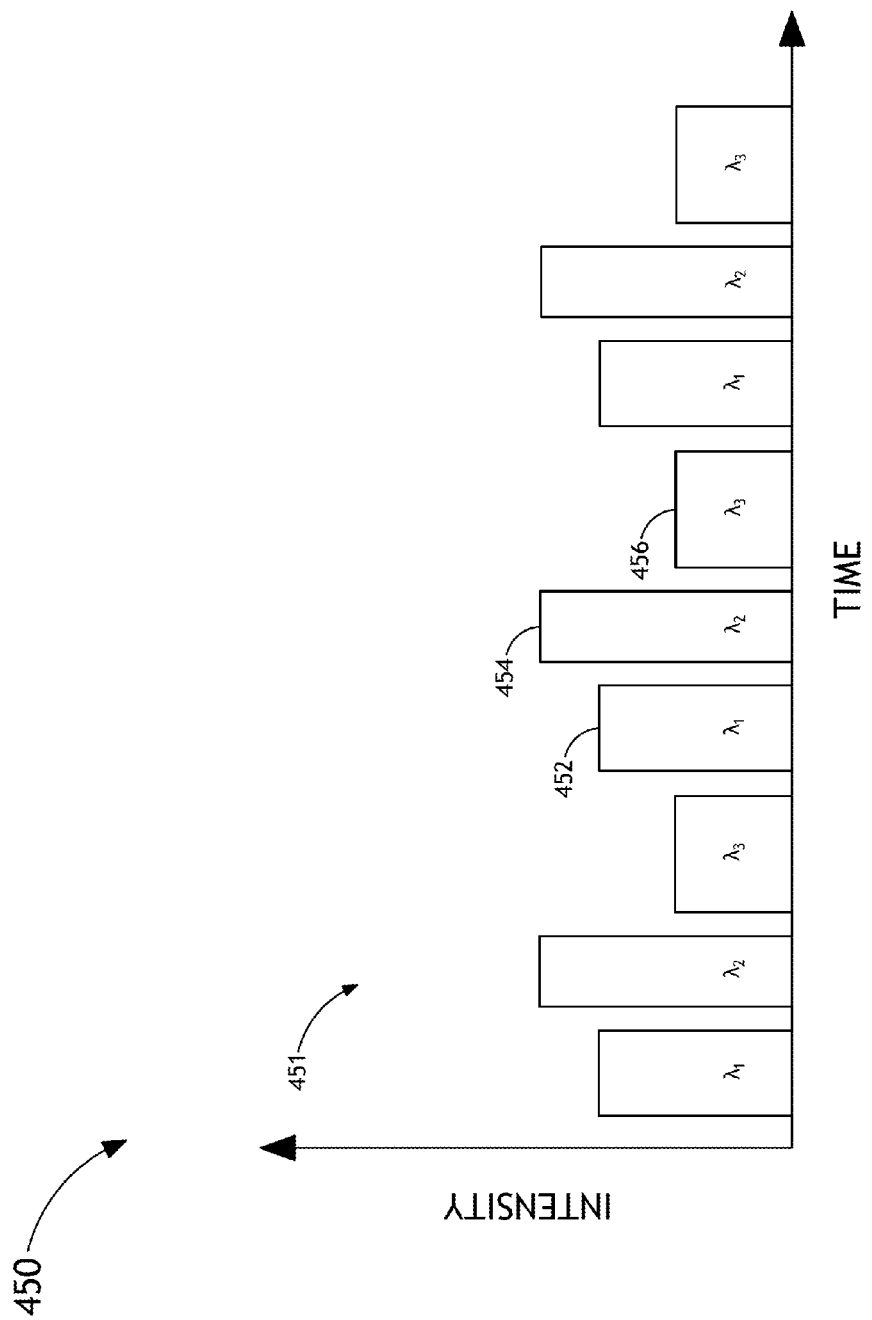
FIG. 4B illustrates a conceptual view of an interleaved pulse train output of multiple illumination sources each of a different wavelength, in accordance with one embodiment of the present invention.

FIG. 4B illustrates a conceptual view of a graph 450 of a set of interleaved waveforms from three illuminations sources of different wavelength $\lambda_1$, $\lambda_2$, and $\lambda_3$. The pulse train 451 depicted in FIG. 4B is representative of either the input drive current of the illumination source or the output intensity of the illumination source for each wavelength (e.g., $\lambda_1, \lambda_2,$ and $\lambda_N$). In this regard, the pulse train 451 may consist of a set of pulses 452 of wavelength $\lambda_1$, a set of pulses 454 of wavelength $\lambda_2$, and up to and including a set of pulses of wavelength $\lambda_N$. It is noted herein that the input drive current (not shown in FIG. 4B), the duty cycle (i.e., width of each pulse for a given wavelength), and output power (i.e., height of each pulse for a given wavelength in FIG. 4B) is in general different for each wavelength waveform and is selected based on the requirements of the given optical metrology system. It is further recognized herein that the drive current may be switched between zero and the nominal peak current or, alternatively, may follow a more complex periodic scheme (e.g., the lower bound may be chosen to be a non-zero current). The frequency, duty cycles, and peak current and power levels of the waveform can be chosen for optimal performance of the illumination sources (e.g., lasers) and other components of the metrology tool 100, such as a beam monitor, the detector (e.g., one or more CCDs), and auto-focus subsystem, and the like. It is further noted that changing the duty cycle and input current may also aid in achieving desired intensity levels and balance for the multiple light sources 402a-402c. It is further recognized that the repetition frequencies of the waveforms of the pulse train 451 may be on the order of 100 Hz. As such, the multi-source repetition frequencies of the present invention are much slower than the single-source modulation frequencies (e.g., RF frequencies) of the illumination source 102 as discussed previously herein. Therefore, control schemes for interleaved color-sequential operation (e.g., 100 Hz frequency range) and for noise/coherence effects reduction (e.g., RF frequencies) may be implemented simultaneously. In this regard, the control system 112 may drive a given illumination source (e.g., 402a-402c) with multiple periodic waveforms operating at significantly different timescales. For example, in addition to the interleaving of waveforms of source 402a, 402b, and 402c, one or more of the sources 402a, 402b or 402c may undergo a fast modulation operation (on the order of RF frequencies) in order to reduce coherence artifacts for the given single source.

In another aspect of the present invention, one or more of the illumination sources 402a-402c may include any broadband illumination source known in the art. In one embodiment, one or more of the illumination sources 402a-402c may include, but are not limited to, a HLS, as described above. In another example, one or more of the illumination sources 402a-402c may include a xenon arc lamp. By yet another example, one or more of the illumination sources 402a-402c may include a deuterium arc lamp. In another embodiment, one or more of the illumination sources 402a-402c may include, but is not limited to, any discharge plasma source known in the art. In yet another embodiment, one or more of the illumination sources 402a-402c may include, but are not limited to, a laser-driven plasma source. In a further embodiment, one or more spectral filters (not shown) may be disposed between the output of one or more broadband filters and the wavelength combiners 404a-404c in order to spectrally filter the spectral output of one or more broadband illumination sources.

In another aspect of the present invention, one or more of the illumination sources 402a-402c may include any narrowband illumination source known in the art. In one embodiment, one or more of the illumination sources 402a-402c may include, but are not limited to, one or more lasers. For instance, one or more of the illumination sources 402a-402c may include, but are not limited to, one or more semiconductor lasers. In another example, one or more of the illumination sources 402a-402c may include, but are not limited to, a diode-pumped solid-state laser. In another example, one or more of the illumination sources 402a-402c may include, but are not limited to, a super continuum laser. In another embodiment, one or more of the illumination sources 402a-402c may include, but are not limited to, one or more light-emitting diodes. It should be recognized by those skilled in the art that the above described illumination sources do not represent limitations, but should merely be interpreted as illustrative. In a general sense, any illumination source capable of producing illumination in the visible, infrared, and ultraviolet spectral ranges are suitable for implementation in one or more of the illumination sources 402a-402c.

It is further recognized herein the set of multiple sources 402a-402c may include a combination of narrowband and broadband sources. For example, one or more of the sources 402a-402c may include a laser source, while one or more of the remaining sources consist of a broadband lamp (e.g., laser produced plasma source) equipped with a fixed or wavelength-switchable spectral filter.

Figure 5:
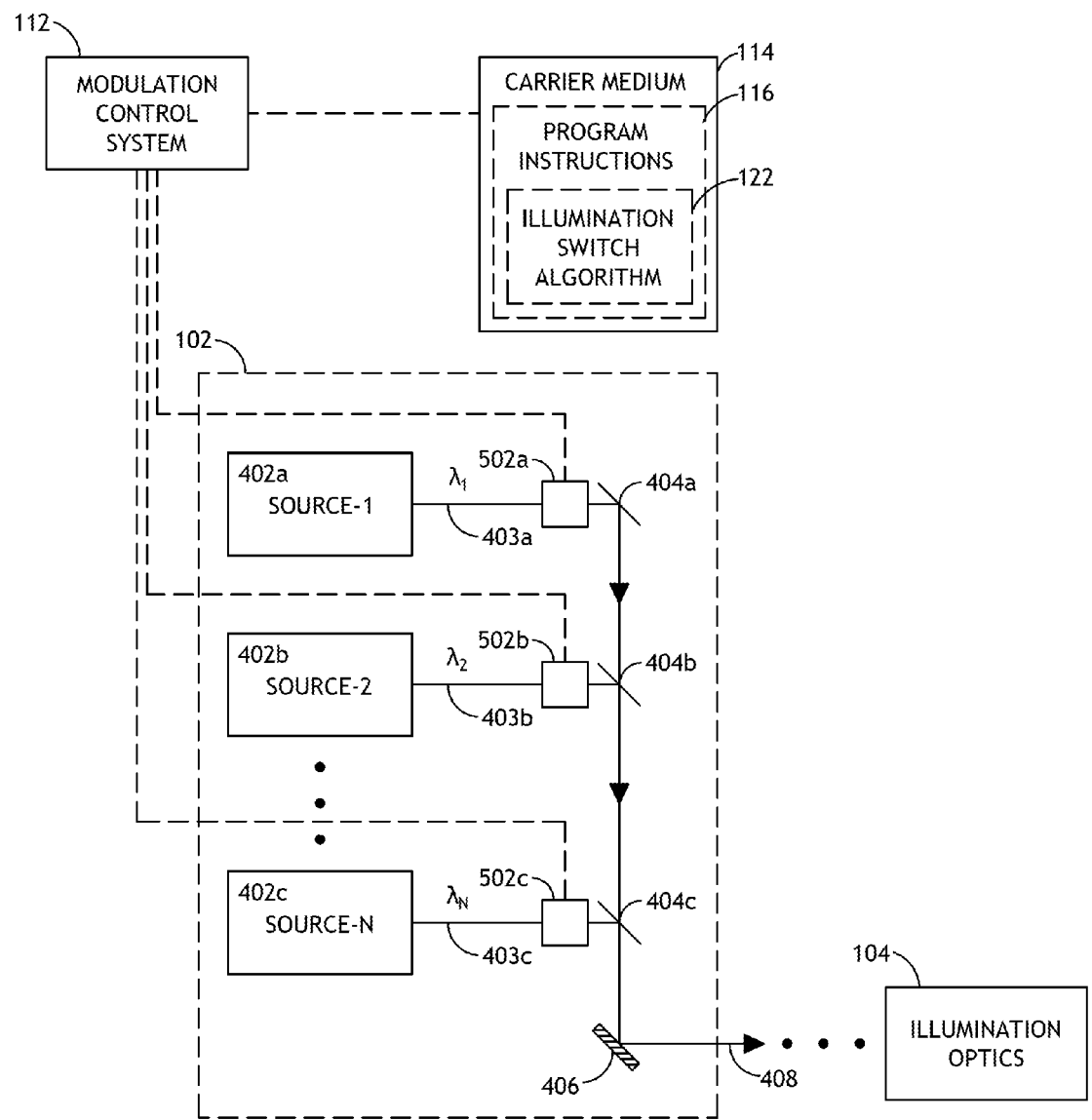
FIG. 5 illustrates a high level schematic view of an optical metrology system equipped with multiple illumination sources each of a different wavelength, whereby intensity is controlled via an intensity switching device, in accordance with one embodiment of the present invention.

FIG. 5 illustrates a multi-source illumination source 102 with intensity switching capabilities, in accordance with an alternative embodiment of the present invention. In one aspect, the multi-source illumination source 102 of the optical metrology tool 100 includes two or more single illumination sources, each single source having a different output wavelength. In an additional aspect, the multi-source illumination source 102 of FIG. 5 includes a set of illumination switching devices 502a, 502b, and 502c. In this regard, the intensity contribution of each source 402a, 402b, and 402c to the combined output beam 408 may be controlled using the illumination switching devices 502a, 502b, and 502c respectively. Further, the modulation control system 112 may be configured to control the illumination switching devices 502a-502c via illumination switching algorithm 122, thereby controlling the intensity of each wavelength component of the combined beam 408. In this manner, the modulation control system 112 may control the waveforms associated with each wavelength $\lambda_1$, $\lambda_2$, and up to and including $\lambda_N$, thereby transmitting a combined waveform of selected frequency, duty cycle, and intensity of each wavelength component.

In one embodiment, the one or more of the illumination switching devices 502a, 502b, and 502c may include, but are not limited to, a Pocket's cell disposed between a first polarizer and a second polarizer. In this regard, the Pocket cell associated with each wavelength channel $\lambda_1$, $\lambda_2$, and $\lambda_N$ may act as a digital ON/OFF intensity switch that is responsive to a transmitted signal from the modulation control signal. In a further embodiment, the switching period of each Pocket's cell may be much shorter than the integration time of the detector 110, obviating the need for phase synchronization between the Pocket's cell and the given source 402a-402c and/or detector 110.

In another embodiment, the one or more of the illumination switching devices 502a, 502b, and 502c may include, but are not limited to, an acousto-optical switching device. In a general sense, any fast optical switching device known in the art.

Figure 6:
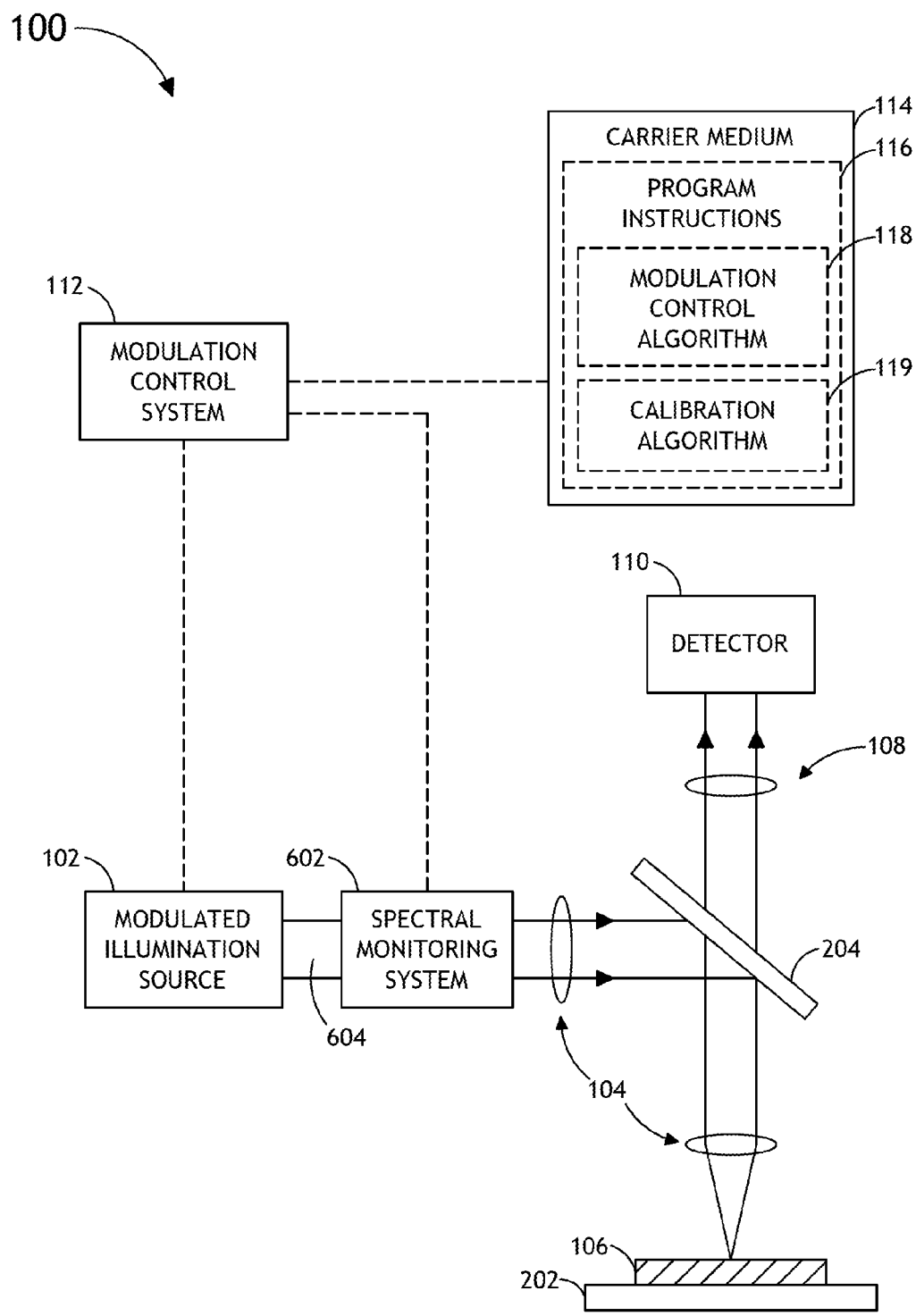
FIG. 6 illustrates a high level schematic view of an optical metrology tool equipped with a spectral monitoring device, in accordance with one embodiment of the present invention.

FIG. 6 illustrates a spectral monitoring system 602 configured to monitor one or more spectral characteristics of the modulatable illumination source 102, in accordance with one embodiment of the present invention. It is recognized herein that in settings where the noise and coherence artifacts have been reduced (i.e., by reducing coherence of illumination) accurate knowledge of the spectral properties of the illumination is desirable. In one embodiment, the spectral monitoring system 602 may be used to monitor peak or centroid wavelength for each illumination source. It is also anticipated that the spectral monitoring system 602 may be particularly useful in the context of drive current modulated diode laser based illumination sources (described previously herein) as proper monitoring of the spectral output of the illumination beam will ensure the coherence length of the given illumination beam is reduced below an acceptable level. In this regard, one or more portions of the spectral monitor system 602 may be disposed along the illumination pathway 604 of the optical metrology tool 100. In this sense, the spectral monitoring system 602 may measure one or more spectral characteristics of the illumination emanating from the modulatable illumination source 102. In one embodiment, the one or more spectral characteristics may include, but are not limited to, intensity spectra over a selected wavelength range, position of one or more spectral peaks of interest (e.g., position of centroid wavelength), full-width half-maximum (FWHM) of a spectral peak of interest, and the like.

In a further embodiment, the spectral monitoring system may be communicatively coupled to the modulation control system 112. In this regard, results of a spectral measurement of illumination in the illumination pathway 604 may be transmitted to the control system 112. In a further embodiment, the modulation control system 112 may store the results of the spectral monitoring process in a memory medium for future use.

In one embodiment, the spectral monitoring system 602 may monitor one or more spectral characteristic of illumination from the illumination source 102 in real-time or near-real-time. For example, the spectral monitoring system 602 may include a spectrometer suitable for real-time measurement of one or more spectral characteristics of illumination from the illumination source 102. For instance, the spectral monitoring system 602 may include, but is not limited to, a grating-based spectrometer. Applicants note that a grating-based spectrometer may be particularly useful in measuring the spectral characteristics (e.g., centroid wavelength) of light sources used for optical metrology tools of this invention.

In another embodiment, the spectral monitoring system 602 may monitor one or more spectral characteristic of illumination from the illumination source 102 for calibration purposes. For example, the spectral monitoring system 602 may measure one or more spectral characteristics of illumination from the illumination source in a tool set-up calibration process. For instance, the spectral monitoring system 602 may measure one or more spectral characteristics of illumination from the illumination source 102 in a tool set-up calibration process, whereby an optical metrology measurement is carried out on a calibration target (i.e., target having known parameters (e.g., known CD, known thin film thickness and/or composition, known overlay, and the like)). Utilizing the results of the metrology measurement (e.g., thickness measurement) and the results of the measured spectral characteristics of the illumination, the control system 112 may carry out a spectral monitoring calibration algorithm 119 stored in the carrier medium 114. The modulation control system 112 may periodically calibrate, or "re-calculate," one or more spectral properties of the illumination from the illumination source 102 based on the measurement of the calibration sample and the measured spectral properties of the illumination. It is further noted that the frequency of spectral calibration may depend on the spectral stability of the given illumination source.

In one embodiment, the calibration sample may consist of a sample having a known thin film thickness. For example, the calibration sample may include, but is not limited to, a sample having a known oxide layer thickness (e.g., a silicon-based W-chip having a known oxide thickness). In this regard, the thickness of the calibration sample may be calibrated during the calibration process carried out by the control system 112. Then, the spectral characteristics of the calibration sample may be periodically monitored use each data channel (e.g., all wavelengths of illumination, polarization states, and the like) of the system 100. Based on the monitoring by the spectral monitoring system 602 the control system 112 may re-calculate the spectral properties (e.g., each wavelength value of the spectrum) of the illumination source 102.

In an additional aspect, the modulation control system 112 may input the results from a measurement of one or more spectral characteristics of a given sample into the sample modeling software of the control system 112. In this regard, the sample modeling software executed by the control system 112 acts to correlate measured data from the sample with a given optical model. The implemented optical model may use as an input the one or more spectral characteristics of the given analyzed sample acquired by the spectral monitoring system 602.

It is noted herein that the spectral monitoring system 602 may include any spectral monitoring/measurement device known in the art. For example, the spectral monitoring system 602 may include, but is not limited to, any spectrometer known in the art (e.g., grating-based spectrometer).

Figure 7A:
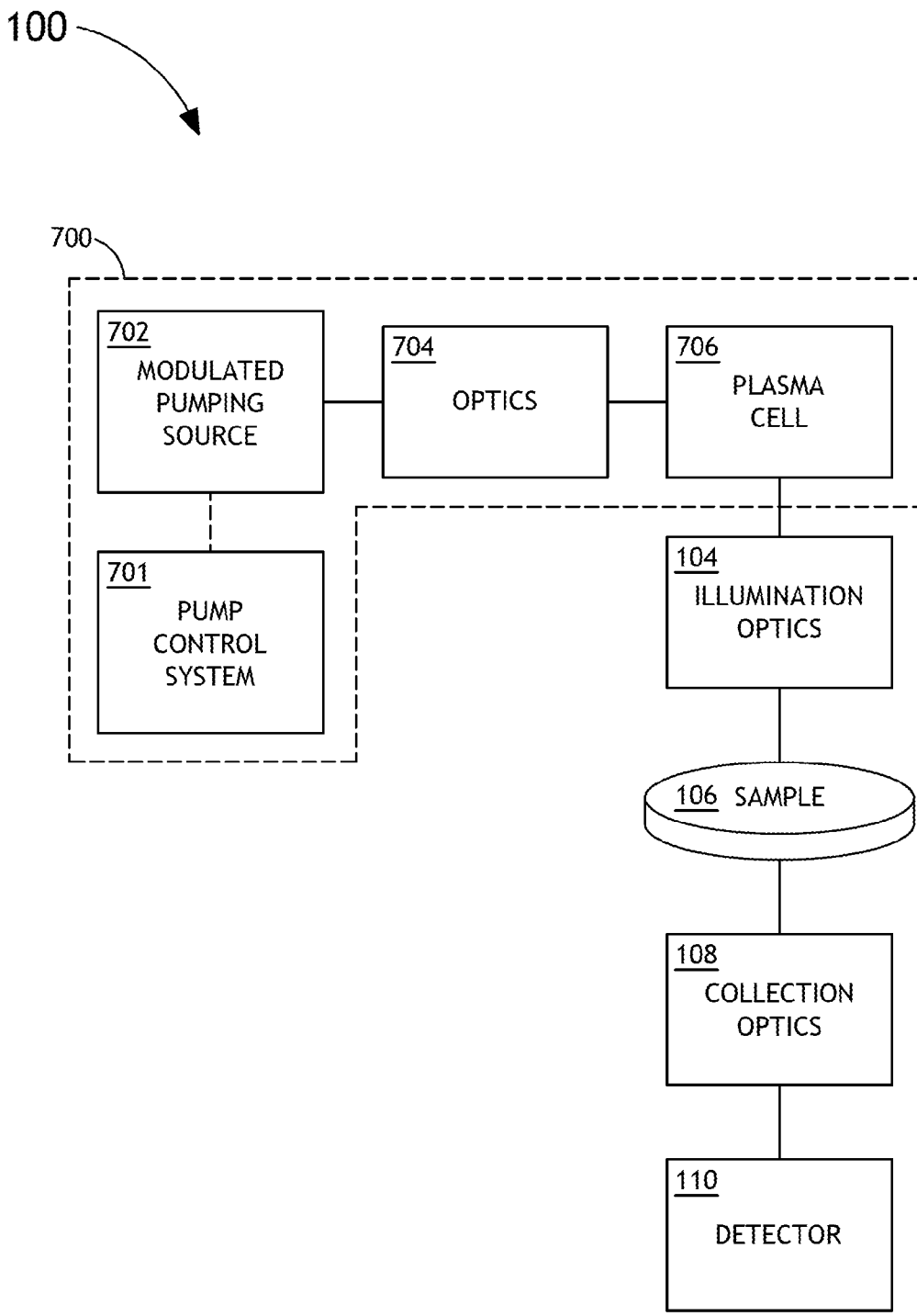
FIG. 7A illustrates a high level block diagram of a laser-pumped plasma based optical metrology tool with a modulated pump source, in accordance with one embodiment of the present invention.

FIG. 7A illustrates a block diagram view of a light-driven plasma illumination subsystem 700 with a modulated pumping source suitable for implementation in the optical metrology tool 100 of the present invention. It is noted herein that operation of plasma sources with pumping sources (e.g., pumping lasers) driven in a constant-current mode may lead to noise levels larger than desirable for optical metrology applications. The present invention is directed to drive current modulation of a pumping laser of a plasma source in order to reduce noise levels in the output illumination of the plasma source. In particular, the pump control system 701 of the light-driven (e.g., laser-driven) illumination subsystem 700 may act to reduce the noise level within a particular frequency bandwidth by modulating the pumping source 702 at frequencies greater than the detector 110 bandwidth. In this regard, the modulation frequency is selected such that the laser modulation does not alias to the detected frequency range of interest.

In one aspect, the plasma-based illumination subsystem 700 of the optical metrology tool 100 may include a modulatable pumping source 702 configured to generate illumination (e.g., generate illumination of a selected wavelength) and a plasma cell 706 suitable for containing a selected gas (e.g., argon, xenon, mercury, and the like). In addition, the subsystem 700 may include a set of optics 704 (e.g., focusing optics, shaping optics, condition optics, and the like) configured to condition and shape the beam emanating from the pumping source 702 and further configured to focus the beam into the volume of gas contained within the bulb of the plasma cell 706. It is noted herein that beam shaping and condition elements of the subsystem 700 may be utilized to optimize, or at least improve, the shape of the beam emanating from the pumping source 702 in order to maximize pumping efficiency (or at least attain a selected level of pumping efficiency) in the plasma cell 706. In addition, the beam shaping optics may be utilized to optimize the shape of the plasma within the plasma cell 706. By focusing light from the pumping source 702 into the volume of gas contained within the plasma cell 706, energy is absorbed by the gas or plasma within the bulb of the plasma cell 706, thereby "pumping" the gas species in order to generate or sustain a plasma.

In a further aspect, broadband illumination emitted by the plasma cell 706 may then be directed to the sample 106 via the illumination optics 104 of the optical metrology tool 100. Then, the collection optics 108 of the metrology tool 100 may direct illumination reflected or scattered from the sample 106 to the detector 110.

The generation of plasma within inert gas species is generally described in U.S. patent application Ser. No. 11/695,348, filed on Apr. 2, 2007; U.S. Pat. No. 7,435,982, issued on Oct. 14, 2008, which are incorporated herein by reference in their entirety. In a general sense, the subsystem 700 should be interpreted to extend to any plasma based light source known in the art.

Figure 7B:
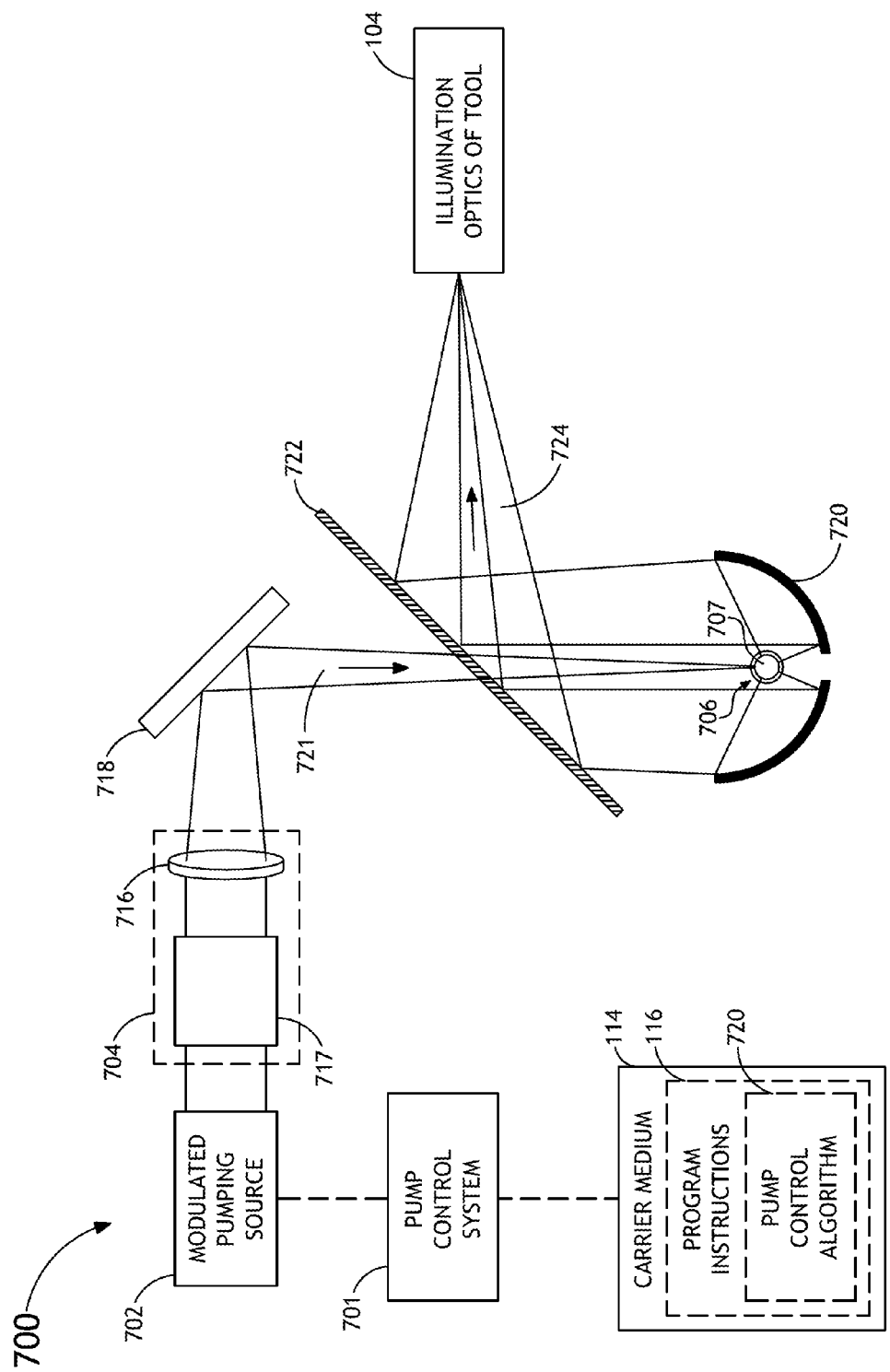
FIG. 7B illustrates a high level schematic view of a laser-pumped plasma based optical metrology tool with a modulated pump source, in accordance with one embodiment of the present invention.

FIG. 7B illustrates a schematic view of the laser-driven illumination subsystem 700, in accordance with one embodiment of the present invention. In one embodiment, the optics 704 of subsystem 700 may include, but are not limited to, beam conditioning/shaping optics 717 configured for conditioning/shaping the beam from the modulated pumping source 702. Further, the optics 704 may include a set of focusing optics 716 suitable for focusing illumination from the pumping source 702 into the volume of gas 707 contained within the bulb of the plasma cell 706.

In an additional embodiment, the subsystem 700 may include a variety of additional optical components. For example, the subsystem 700 may include, but is not limited to, a steering mirror 718 suitable for directing illumination 721 from the modulated pumping source 702 toward the plasma cell 706. In a further example, the subsystem 700 may include, but is not limited to, a beam splitter/dichroic mirror 722 suitable for transmitting illumination from the pumping source 702 to the plasma cell 706 and further suitable for reflecting broadband illumination emitted by the plasma cell 706 (and directed by the ellipse 720) along an output path 724 toward a set of illumination optics 104 of the optical metrology tool 100 (described previously herein).

Applicant notes that the above description of the laser-driven illumination subsystem 700 is in no way limiting and should be interpreted merely as illustrative. It is noted herein that numerous laser-driven plasma illumination subsystems suitable for implementation in the present invention.

For example, the ellipse 720 may also be configured to act as a focusing element for illumination emanating from the pumping source 702, whereby the ellipse 720 may act to focus illumination 721 into the volume of gas 707 of the plasma cell 706. In this regard, the ellipse 720 may be configured to both focus laser illumination from the pumping source 702 into the plasma cell 706 as well as directing broadband emissions from the plasma cell 706 toward the downstream illumination optics 104 of the metrology tool 100. In this embodiment, the subsystem 700 may also include a collimator (not shown) configured to collimate illumination emanating from the pumping source 702.

By way of another example, the system 700 may be configured for separating the illumination 721 emitted by the pumping source 702 from the broadband emissions 724 emitted by the plasma cell 706 without the need for beam splitter 722. In this regard, the illumination optics 104 of the optical metrology tool 100 may be configured to receive broadband emissions 724 directly from the plasma cell 706. For instance, the pumping source NA 721 may be separated from the plasma emission NA 724, whereby the pumping source NA 721 is vertically oriented, while the plasma emissions are collected along a horizontal path.

In an additional aspect, the illumination subsystem 700 includes a pump control system 701 communicatively coupled to the modulatable pumping source 702, wherein the modulation control system 701 is configured to modulate a drive current of the modulatable pumping source 702 at a selected modulation frequency in order to produce time-varying characteristics within the plasma/gas volume in the plasma cell 706. For example, the time-varying characteristics may include, but are not limited to, time-varying thermal distributions within the plasma/gas volume in the plasma cell 706. In a further aspect, the pump control system 701 may control the modulatable pumping source 702 via pump control algorithm 720 stored as a set of program instructions 116 in carrier medium 114.

In one embodiment, the modulatable pumping source 702 of the illumination subsystem 700 includes, but is not limited to, one or more lasers. Applicant further notes that for the purposes of clarity the various components of the optical metrology tool 100 residing downstream from the illumination optics 104 are not depicted in FIG. 7B. Applicant notes, however, that the various components and subsystems of the optical metrology tool 100 as described previously herein should be interpreted to extend to the light-driven plasma source depicted in FIGS. 7A and 7B. In addition, the light-sustained plasma source depicted in FIGS. 7A and 7B may be implemented in a reflectometer, scatterometer, ellipsometer, or spectrometer configuration as discussed previously herein.

It is noted herein that the frequency of modulation of the pumping source 702 should be sufficiently above the Nyquist frequency of the detector electronics of the optical metrology tool 100 in order to minimize aliasing in the detector 110.

In addition, the depth of modulation must be selected such that significant characteristic variation is achieved within the plasma of the plasma cell 706 without reducing the power density within the plasma to a level where the plasma is no longer sustainable. In a further aspect, the pump control system 701 may act to modulate the drive current of the laser pumping source 702, thereby modulating the pump laser intensity and wavelength. Modulation in intensity and wavelength in the light output of the pumping source 702 may act to generate oscillating characteristics (e.g., temperature distribution) within the plasma of the plasma cell 706. Since the plasma emissions from the plasma cell 706 typically pass through numerous optical components, including one or more apertures, which limit the spatial extent of the plasma imaged through the optical system, the modulation of the spatial distribution of the plasma source may contribute on the same order as the modulation of the spatially integrated power collected from the light source. Applicants have found a significant reduction in noise level across a wide range of modulation amplitudes for a modulation frequency of approximately 20 kHz to 40 kHz. Applicants have also shown that square wave and sine wave modulation of the pumping source 702 are effective in noise level reduction. Applicants note that the frequency range and types of waveforms provided above are in no way limiting and are provided merely for purposes of illustration. It is anticipated that a variety of modulation waveforms and frequency ranges are within the scope of the present invention.

It is further noted herein that by controlling the plasma characteristics as described above and integrating over multiple modulation periods for each detector sample the illumination subsystem 700 may act to reduce the effects of randomness on the overall noise level of the overall optical metrology tool 100.

It is further contemplated that each of the embodiments of the method described above may include any other step(s) of any other method(s) described herein. In addition, each of the embodiments of the method described above may be performed by any of the systems described herein.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims. Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. An optical metrology tool, comprising:
    a modulatable illumination source configured to illuminate a surface of a sample disposed on a sample stage;
    a set of illumination optics configured to direct illumination from the modulated illumination source to the surface of the sample;
    a set of collection optics;
    a detector configured to detect at least a portion of illumination emanating from a surface of the sample, wherein the set of collection optics is configured to direct illumination from the surface of the sample to the detector wherein the modulatable illumination source, the detector, the set of illumination optics, and the set of collections optics are positioned to perform optical metrology on the sample; and
    a modulation control system communicatively coupled to the modulatable illumination source, wherein the modulation control system is configured to modulate a drive current of the modulatable illumination source at a selected modulation frequency, wherein the modulatable illumination source, in response to the modulation control system, modulates the illumination from the modulatable illumination source so as to suppress one or more coherence features within the illumination relative to illumination from the modulatable illumination source in an unmodulated state.

2. The optical metrology tool of claim 1, wherein the selected modulation frequency comprises:
    a modulation frequency suitable for generating illumination having a selected fringe visibility curve.

3. The optical metrology tool of claim 2, wherein the modulation frequency suitable for generating illumination having a selected fringe visibility curve comprises:
    a modulation frequency suitable for generating illumination having a fringe visibility curve suitable for achieving coherence artifacts below a selected tolerance level.

4. The optical metrology tool of claim 2, wherein the selected fringe visibility curve is configured to suppress generation of interference fringes having an intensity above a selected level.

5. The optical metrology tool of claim 2, wherein the selected fringe visibility curve is substantially different from a fringe visibility curve of the illumination source in an unmodulated state.

6. The optical metrology tool of claim 1, wherein the selected modulation frequency comprises:

a modulation frequency suitable for generating illumination having a set of intensity peaks positioned at distances different from a characteristic optical path length of the optical metrology tool.

7. The optical metrology tool of claim 6, wherein the characteristic optical path length of the optical metrology tool comprises:
a distance between a first reflecting surface of the optical metrology tool and a second reflecting surface of the optical metrology tool.

8. The optical metrology tool of claim 1, wherein the selected modulation frequency suitable for generating illumination having a selected coherence feature comprises:
a modulation frequency suitable for generating illumination having a coherence length below a selected length.

9. The optical metrology tool of claim 8, wherein the selected length comprises:
a characteristic optical path length of the optical metrology tool.

10. The optical metrology tool of claim 9, wherein the characteristic optical path length of the optical metrology tool comprises:
a distance between a first reflecting surface of the optical metrology tool and a second reflecting surface of the optical metrology tool.

11. The optical metrology tool of claim 8, wherein the selected length comprises:
a coherence length of the modulatable illumination source in an unmodulated state.

12. The optical metrology tool of claim 1, wherein the optical metrology tool is configured to perform at least one of critical dimension metrology, thin film metrology, and overlay metrology.

13. The optical metrology tool of claim 1, wherein the modulatable illumination source comprises:
one or more lasers.

14. The optical metrology tool of claim 13, wherein the one or more lasers comprise:
one or more semiconductor diode lasers.

15. The optical metrology tool of claim 13, wherein the one or more lasers comprise:
one or more diode-pumped solid-state lasers.

16. The optical metrology tool of claim 13, wherein the one or more lasers comprise:
one or more super continuum lasers.

17. The optical metrology tool of claim 1, wherein the selected modulation frequency is in the radio frequency (RF) range.

18. The optical metrology tool of claim 1, wherein the modulatable illumination source, the detector, the set of illumination optics, and the set of collections optics are configured in a reflectometry geometry.

19. The optical metrology tool of claim 18, wherein the modulatable illumination source, the detector, the set of illumination optics, and the set of collections optics are configured in at least one of an angle-resolved reflectometry geometry and a spectroscopic reflectometry geometry.

20. The optical metrology tool of claim 1, wherein the modulatable illumination source, the detector, the set of illumination optics, and the set of collections optics are configured in a scatterometry geometry.

21. The optical metrology tool of claim 1, wherein the modulatable illumination source, the detector, the set of illumination optics, and the set of collections optics are configured in an ellipsometry geometry.

22. The optical metrology tool of claim 1, wherein the detector comprises:
at least one of a CCD array, a CMOS array, one-dimensional photodiode array, and a two-dimensional photodiode array.

23. The optical metrology tool of claim 1, wherein the detector is synchronized with the control system.

24. The optical metrology tool of claim 1, further comprising:
a spectral monitoring system configured to monitor one or more spectral characteristics of illumination from the modulatable illumination source, the spectral monitoring system further configured to transmit a signal indicative of the one or more spectral characteristics to the control system.

* * * * *